US011047868B2

(12) United States Patent
Zimring

(10) Patent No.: US 11,047,868 B2
(45) Date of Patent: *Jun. 29, 2021

(54) BIOCHEMICAL MARKERS OF RED BLOOD CELL STORAGE AND TOXICITY

(71) Applicant: Bloodworks, Seattle, WA (US)

(72) Inventor: James Charles Zimring, Seattle, WA (US)

(73) Assignee: Bloodworks, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/750,984

(22) Filed: Jan. 23, 2020

(65) Prior Publication Data

US 2020/0158740 A1 May 21, 2020

Related U.S. Application Data

(63) Continuation of application No. 16/425,768, filed on May 29, 2019, now Pat. No. 10,578,627, which is a continuation of application No. 15/872,748, filed on Jan. 16, 2018, now Pat. No. 10,345,316, which is a continuation of application No. 15/476,837, filed on Mar. 31, 2017, now Pat. No. 9,903,876, which is a continuation of application No. 14/012,885, filed on Aug. 28, 2013, now Pat. No. 9,638,687.

(60) Provisional application No. 61/693,956, filed on Aug. 28, 2012.

(51) Int. Cl.
| G01N 33/50 | (2006.01) |
| G01N 33/80 | (2006.01) |
| G01N 33/53 | (2006.01) |

(52) U.S. Cl.
CPC ......... *G01N 33/80* (2013.01); *G01N 33/5005* (2013.01); *G01N 33/53* (2013.01); *G01N 2800/7066* (2013.01)

(58) Field of Classification Search
None
See application file for complete search history.

(56) References Cited

U.S. PATENT DOCUMENTS

| 9,638,687 | B2 | 5/2017 | Zimring | |
| 9,903,876 | B2 | 2/2018 | Zimring | |
| 10,345,316 | B2 * | 7/2019 | Zimring | ............... G01N 33/80 |
| 10,578,627 | B2 * | 3/2020 | Zimring | ............... G01N 33/53 |
| 2018/0238911 | A1 | 8/2018 | Zimring | |
| 2019/0285655 | A1 | 9/2019 | Zimring | |

OTHER PUBLICATIONS

Aoki and Narumiya, "Prostaglandins and chronic inflammation," Trends Pharmacol. Sci., vol. 33, No. 6, 2012, pp. 304-311.
Dern and Wiorkowski, "Studies on the preservation of human blood. IV. The hereditary component of pre- and poststorage erythrocyte adenosine triphosphate levels," J. Lab. Clin. Med., vol. 73, No. 6, 1969, pp. 1019-1029.
Di Gennaro and Haeggstrom, "The leukotrienes: immune-modulating lipid mediators of disease," Adv. Immunol., vol. 116, 2012, pp. 51-92.
Dominici et al., "Transgenic mice with pancellular enhanced green fluorescent protein expression in primitive hematopoietic cells and all blood cell progeny," Genesis, vol. 42, 2005, pp. 17-22.
Dumaswala, et al., "Glutathione loading prevents free radical injury in red blood cells after storage," Free Radic. Res., vol. 33, No. 5, 2000, pp. 517-529.
Dumaswala, et al., "Glutathione protects chemokine-scavenging and antioxidative defense functions in human RBCs," Am. J. Physiol. Cell Physiol., vol. 280, 2001, pp. C867-C873.
Dumaswala, et al., "Protein and lipid oxidation of banked human erythrocytes: role of glutathione," Free Radic. Biol. Med., vol. 27, No. 9-10, 1999, pp. 1041-1049.
Dumont and AuBuchon, "Evaluation of proposed FDA criteria for the evaluation of radiolabeled red cell recovery trials," Transfusion, vol. 48, No. 6, 2008, pp. 1053-1060.
Office Action dated Jun. 4, 2018 for European patent application No. 13832087.4, a counterpart foreign application of U.S. Pat. No. 9,638,687, 4 pages, dated Jun. 4, 2018.
Fergusson, et al., "Effect of fresh red blood cell transfusions on clinical outcomes in premature, very low-birth-weight infants: the ARIPI randomized trial," JAMA, vol. 308, No. 14, 2012, pp. 1443-1451.
Gilson, et al., "A novel mouse model of red blood cell storage and posttransfusion in vivo survival," Transfusion, vol. 49, No. 8, 2009, pp. 1546-1553.
Hess, "Red cell changes during storage," Transfus. Apher. Sci., vol. 43, No. 1, 2010, pp. 51-59.
Hess, "Red cell storage," J. Proteomics, vol. 73, No. 3, 2010, pp. 368-373.
Hess, "Scientific problems in the regulation of red blood cell products," Transfusion, vol. 52, No. 8, 2012, pp. 1827-1835.
Hod and Spitalnik, "Harmful effects of transfusion of older stored red blood cells: iron and inflammation," Transfusion, vol. 51, No. 4, 2011, pp. 881-885.
Hod and Spitalnik, "Stored red blood cell transfusions: Iron, inflammation, immunity, and infection," Transfus. Clin. Biol., vol. 19, No. 3, 2012, pp. 84-89.
Hod, et al., "Transfusion of human volunteers with older, stored red blood cells produces extravascular hemolysis and circulating non-transferrin-bound iron," Blood, vol. 118, No. 25, 2011, pp. 6675-6682.
Hod, et al., "Transfusion of red blood cells after prolonged storage produces harmful effects that are mediated by iron and inflammation," Blood, vol. 115, No. 21, 2010, pp. 4284-4292.
Hoffmann-Fezer, et al., "Direct in vivo biotinylation of erythrocytes as an assay for red cell survival studies," Ann. Hematol., vol. 63, No. 4, 1991, pp. 214-217.
Klein HG, Anstee DJ. Mollisoni's Blood Transfusion in Clinical Medicine. Malden, Mass: Blackwell Publishing Inc, 2005.

(Continued)

*Primary Examiner* — Gary Counts
(74) *Attorney, Agent, or Firm* — Lee & Hayes PC; C. Rachal Winger; Thu Nguyen

(57) ABSTRACT

Compositions and methods for determining post-transfusion survival or toxicity of red blood cells and the suitability of red blood cell units for transfusion by measuring the levels of one or more markers in a red blood cell sample are provided.

9 Claims, 6 Drawing Sheets

(56) References Cited

OTHER PUBLICATIONS

Kor, et al., "Red blood cell storage lesion," Bosn. J. Basic Med. Sci., vol. 9 Suppl 1, 2009, pp. 21-27.

Kruckeberg, et al., "Genetic differences in hemoglobin influence on erythrocyte oxidative stress hemolysis," Blood, vol. 70, No. 4, 1987, pp. 909-914.

Lacroix, et al., "The Age of Blood Evaluation (ABLE) randomized controlled trial: study design," Transfus. Med. Rev., vol. 25, No. 3, 2011, pp. 197-205.

Mouse Phenome Database [monograph on the internet]. 2012. Available from: http://phenoma.jax.org/.

Office action for U.S. Appl. No. 15/329,486, dated May 1, 2019, 11 pages, dated May 1, 2019.

Office action for U.S. Appl. No. 15/872,748, dated Nov. 26, 2018, 7 pages, dated Nov. 26, 2018.

Office Action for U.S. Appl. No. 16/425,768, dated Jul. 2, 2019, 6 pages.

Pratico and Dogne, "Vascular biology of eicosanoids and atherogenesis," Expert Rev. Cardiovasc. Ther., vol. 7, No. 9, 2009, pp. 1079-1089.

Silliman, "Lipids: free fatty acids, eicosanoids, and lysophospholipids and the pro-inflammatory effects of transfusion," ASH Meeting, Scientific Program, 2012, SCI-48.

Silliman, et al., "Identification of lipids that accumulate during the routine storage of prestorage leukoreduced red blood cells and cause acute lung injury," Transfusion, vol. 51, 2011, pp. 2549-2554.

Soga, et al., "Differential metabolomics reveals ophthalmic acid as an oxidative stress biomarker indicating hepatic glutathione consumption," J. Biol. Chem., vol. 281, No. 24, 2006, pp. 16768-16776.

Steiner, et al., "Addressing the question of the effect of RBC storage on clinical outcomes: the Red Cell Storage Study (RECESS) (Section 7)," Transfus. Apher. Sci., vol. 43, No. 1, 2010, pp. 107-116.

Tissot, et al., "Analysis and clinical relevance of microparticles from red blood cells," Curr. Opin. Hematol., vol. 17, No. 6, 2010, pp. 571-577.

Van de Watering, "Red cell storage and prognosis," Vox Sang., vol. 100, No. 1, 2011, pp. 36-45.

Van de Watering, et al., "Pitfalls in the current published observational literature on the effects of red blood cell storage," Transfusion, vol. 51, No. 8, 2011, pp. 1847-1854.

\* cited by examiner

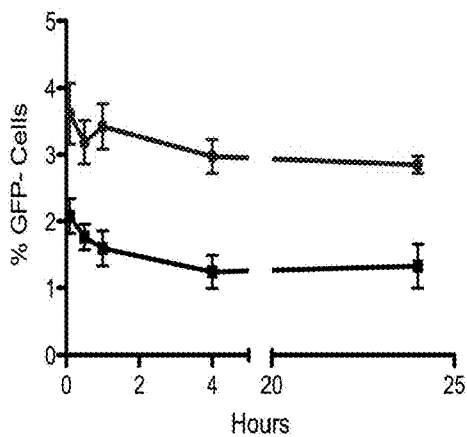
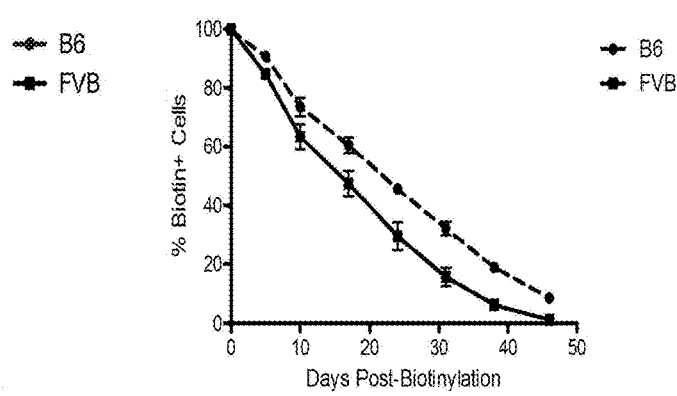
FIG. 1A
FIG. 1B
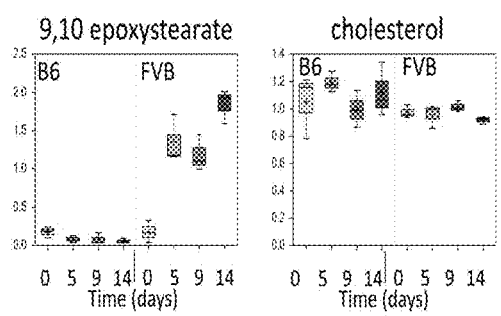
FIG. 1C
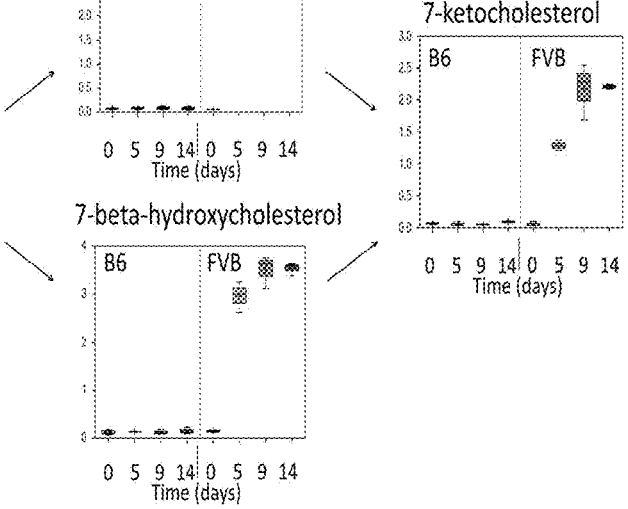
FIG. 1D
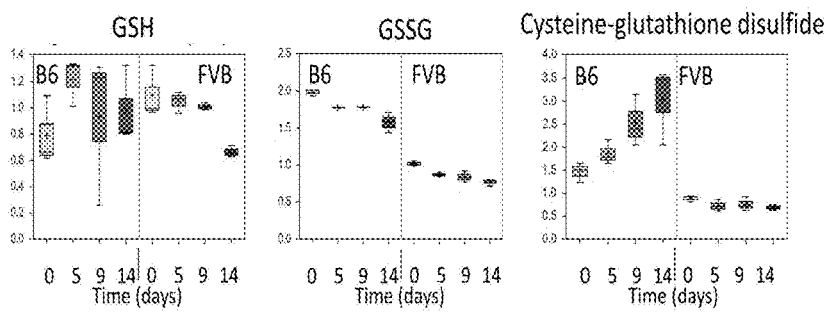
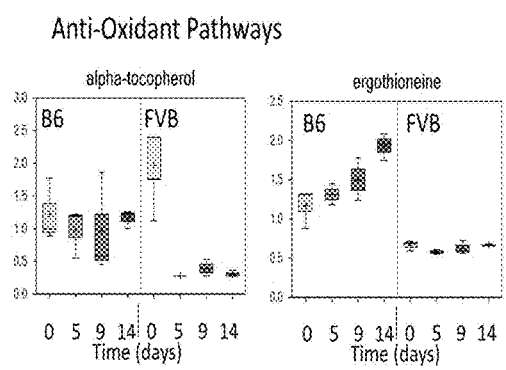
FIG. 1E

BIOCHEMICAL MARKERS OF RED BLOOD CELL STORAGE AND TOXICITY

CROSS REFERENCE TO RELATED APPLICATIONS

This application is a continuation of U.S. patent application Ser. No. 16/425,768, filed May 29, 2019, now U.S. Pat. No. 10,578,627, which is a continuation of U.S. patent application Ser. No. 15/872,748, filed Jan. 16, 2018, now U.S. Pat. No. 10,345,316, which is a continuation of U.S. patent application Ser. No. 15/476,837, filed Mar. 31, 2017, now U.S. Pat. No. 9,903,876, which is a continuation of U.S. patent application Ser. No. 14/012,885, filed Aug. 28, 2013, now U.S. Pat. No. 9,638,687, which claims the benefit of U.S. Provisional Application No. 61/693,956, filed Aug. 28, 2012, each of which is hereby incorporated by reference in its entirety.

STATEMENT REGARDING FEDERALLY SPONSORED RESEARCH OR DEVELOPMENT

This invention was made with government support under Grant No. NIH R01 HL092977, awarded by the National Institutes of Health. The government has certain rights in the invention.

FIELD

The invention relates to compositions and methods for determining post-transfusion survival and toxicity of red blood cell (RBC) units by measuring the levels of one or more markers in a RBC sample.

BACKGROUND

In excess of 15,000,000 units of red blood cells (RBCs) are transfused in the United States each year into an excess of 5,000,000 patients (approximately 1/70 Americans). Currently, there are only 3 quality control measures utilized prior to release of a unit of RBCs: 1) the absence of screened pathogens, 2) compatibility with the patient, 3) storage history at 4° C. FDA guidelines for RBC storage require that stored RBCs (up to 42 days) have less than 1% hemolysis and have 75% 24 hour post-transfusion survival. However, it has been known for decades that RBCs store differently as a function of factors intrinsic to the donor. For example, RBCs from some donors have only 30-40% 24 hour post-transfusion survival, and this is consistently found with units from such donors. However, the factors that regulate whether the blood from a given donor stores well or poorly is poorly understood. For this reason, currently, there are no quality control measures regarding the extent to which a transfused unit of RBCs will survive post-transfusion.

This is a medical problem for two main reasons. First, RBCs that survive poorly post-transfusion result in a less efficacious product from the standpoint of RBC replacement. However, even more important is the notion that RBCs that are cleared from circulation represent a toxic insult to the recipient, which may result in morbidity and/or mortality. A second issue is what biochemical markers may predict RBCs that are going to be toxic from pathways other than simple RBC clearance. It has been described that eicosanoids can accumulate in stored human RBCs, but they can be difficult to detect.

There are currently no existing techniques to predict post-transfusion survival of RBC units or toxicity of said units. Thus, the present disclosure satisfies these and other needs. Disclosed herein is a method for assessing a RBC unit (prior to transfusion) allowing the prediction of its post-transfusion survival and toxicity. Specifically, biochemical markers that predict if RBCs will survive well post-transfusion or will be toxic are presented herein.

SUMMARY

Described herein are compositions and methods for determining post-transfusion survival and toxicity of a RBC unit by measuring the levels of one or more markers in a RBC sample.

In a first aspect, disclosed herein is a method of determining post-transfusion survival of red blood cells (RBC) prior to transfusion, the method comprising the steps of: a) measuring the levels of one or more markers in a RBC sample selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13,14-dihydro-15-keto-prostaglandin E2, and the reticulocyte count of a blood donor at the time of donation; b) comparing the level of the one or more markers in the RBC sample with the level of the one or more markers present in a control sample, wherein a higher or lower level of the one or more markers in the RBC sample is indicative of a lower RBC storage quality.

In a second aspect, disclosed herein is a method of determining the suitability of a red blood cell (RBC) unit for transfusion, the method comprising the steps of: a) measuring the levels of one or more markers in a RBC sample selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13,14-dihydro-15-keto-prostaglandin E2, and the reticulocyte count of a blood donor at the time of donation; b) comparing the level of the one or more markers in the RBC sample with the level of the one or more markers present in a control sample, wherein a higher or lower level of the one or more markers in the RBC sample is indicative of a lower suitability for transfusion.

In various embodiments of the first and second aspects, the measurement is performed at the time of collection of the RBC sample.

In various embodiments of the first and second aspects, the measurement is performed during the time of storage of the RBC sample.

In various embodiments of the first and second aspects, the measurement is performed by mass spectrometry. In various embodiments, the mass spectrometry is gas-chromatography/mass spectrometry (GC/MS) or liquid chromatography-tandem mass spectrometry (LC/MS/MS).

In various embodiments of the first and second aspects, the measurement is performed by enzymatic assay.

In various embodiments of the first and second aspects, the measurement is performed by ELISA.

In various embodiments of the first and second aspects, the level of the one or more marker is 2-200 fold higher than in the control sample.

In a third aspect, disclosed herein is method for determining RBC storage quality, the method comprising the steps of: obtaining a dataset associated with a sample of stored blood, wherein the dataset comprises at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; analyzing the dataset to determine data for the at least one marker, wherein the data is positively correlated or negatively correlated with RBC storage quality of the sample of stored blood.

In a fourth aspect, disclosed herein is method for determining RBC storage quality, the method comprising the steps of: obtaining a sample of stored blood, wherein the sample comprises at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; contacting the sample with a reagent; generating a complex between the reagent and the at least one marker; detecting the complex to obtain a dataset associated with the sample, wherein the dataset comprises expression or activity level data for the at least one marker; and analyzing the expression or activity level data for the at least one marker, wherein the expression or activity level of the at least one marker is positively correlated or negatively correlated with RBC storage quality.

In a fifth aspect, disclosed herein is computer-implemented method for determining RBC storage quality, the method comprising the steps of: storing, in a storage memory, a dataset associated with a stored blood sample, wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; and analyzing, by a computer processor, the dataset to determine the expression or activity levels of the at least one marker, wherein the expression or activity levels are positively correlated or negatively correlated with RBC storage quality.

In a sixth aspect, disclosed herein is system for determining RBC storage quality, the system comprising: a storage memory for storing a dataset associated with a stored blood sample, wherein the dataset comprises data for at least one marker, wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; and a processor communicatively coupled to the storage memory for analyzing the dataset to determine the activity or expression levels of the at least one marker, wherein the activity or expression levels are positively correlated or negatively correlated with RBC storage quality.

In a seventh aspect, disclosed herein is computer-readable storage medium storing computer-executable program code, the program code comprising: program code for storing a dataset associated with a stored blood sample, wherein the dataset comprises data for at least one marker, wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; and program code for analyzing the dataset to determine the activity or expression levels of the at least one marker, wherein the activity or expression levels of the markers are positively correlated or negatively correlated with RBC storage quality.

In an eighth aspect, disclosed herein is method for predicting a negative transfusion outcome, the method comprising the steps of: obtaining a dataset associated with a sample of stored blood, wherein the dataset comprises at least one marker, wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; analyzing the dataset to determine data for the at least one marker, wherein the data is positively correlated or negatively correlated with a negative transfusion outcome if the blood sample is transfused into a patient.

In a ninth aspect, disclosed herein is method for predicting a negative transfusion outcome, the method comprising the steps of: obtaining a sample of stored blood, wherein the sample comprises at least one marker, wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; contacting the sample with a reagent; generating a complex between the reagent and the at least one marker; detecting the complex to obtain a dataset associated with the sample, wherein the dataset comprises expression or activity level data for the at least one marker; and analyzing the expression or activity level data for the markers, wherein the expression or activity level of the at least one marker is positively correlated or negatively correlated with a negative transfusion outcome if the blood sample is transfused into a patient.

In a tenth aspect, disclosed herein is computer-implemented method for predicting a negative transfusion outcome, the method comprising the steps of: storing, in a storage memory, a dataset associated with a stored blood sample, wherein the dataset comprises data for at least one marker wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; and analyzing, by a computer processor, the dataset to determine the expression or activity levels of the at least one marker, wherein the expression or activity levels are positively correlated or negatively correlated with a negative transfusion outcome if the blood sample is transfused into a patient.

In an eleventh aspect, disclosed herein is system for predicting a negative transfusion outcome, the system comprising: a storage memory for storing a dataset associated with a stored blood sample, wherein the dataset comprises data for at least one marker, wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; and a processor communicatively coupled to the storage memory for analyzing the dataset to determine the activity or expression levels of the at least one marker, wherein the activity or expression levels are positively correlated or negatively correlated with a negative transfusion outcome if the blood sample is transfused into a patient.

In a twelfth aspect, disclosed herein is computer-readable storage medium storing computer-executable program code, the program code comprising: program code for storing a dataset associated with a stored blood sample, wherein the dataset comprises data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; and program code for analyzing the dataset to determine the activity or expression levels of the at least one marker, wherein the activity or expression levels of the markers are positively correlated or negatively correlated with a negative transfusion outcome if the blood sample is transfused into a patient.

In various embodiments of the above aspects, the dataset is obtained at the time of collection of the RBC sample.

In various embodiments of the above aspects, the dataset is obtained during the time of storage of the RBC sample.

In various embodiments of the above aspects, the dataset is obtained by mass spectrometry.

In various embodiments of the above aspects, the mass spectrometry is gas-chromatography/mass spectrometry (GC/MS) or liquid chromatography-tandem mass spectrometry (LC/MS/MS).

In various embodiments of the above aspects, the dataset is obtained by enzymatic assay.

In various embodiments of the above aspects, the dataset is obtained by ELISA.

In a thirteenth aspect, disclosed herein is kit for use in predicting a negative transfusion outcome or red blood cell (RBC) storage quality, the kit comprising: a set of reagents comprising a plurality of reagents for determining from a stored blood sample data for at least one marker, selected from the group consisting of Cytidine, 5-Methylcytidine, N4-acetylcytidine, 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, 13, 14-dihydro-15-keto-prostaglandin E2, and the reticulocyte count of a blood donor at the time of donation; and instructions for using the plurality of reagents to determine data from the stored blood sample.

BRIEF DESCRIPTION OF THE DRAWINGS

FIGS. 1A-1E. Post-Transfusion Recovery of Stored Murine RBC units, Endogenous RBC Lifespan, and Metabolomic Analysis of Markers of Oxidative Stress During RBC storage. Murine RBCs were collected and stored (as described in Example 1) for 14 days, and then transfused into H2-K$^b$ GFP mice that express transgenic GFP on all hematopoietic cells, including RBCs. (FIG. 1A) Peripheral blood of recipient mice was sampled at indicated times post-transfusion and recovery of transfused, stored RBCs was determined by flow cytometric enumeration of GFP-negative RBCs. (FIG. 1B) B6 or FVB mice underwent biotinylation in vivo until 100% of their RBCs were avidin reactive. Peripheral blood samples were then stained with avidin-APC at the indicated time points and the percentage of avidin-reactive RBCs was enumerated, which allowed a determination of endogenous RBC lifespan. (FIGS. 1C-1E) Aliquots of stored RBC units obtained from FVB and B6 mouse donors were frozen at the indicated time points and were then analyzed by GC/MS and LC/MS/MS, as appropriate (as described in Example 1). Results are reported for products of lipid peroxidation (FIG. 1C), for glutathione pathway components (FIG. 1D), and for two natural antioxidants (FIG. 1E). These metabolomic data represent the combined results from 3 separate experiments; in each experiment, post-transfusion recovery was determined at Day 14 of storage, with similar results to those in FIG. 1A in each case.

DETAILED DESCRIPTION

Figure 2:
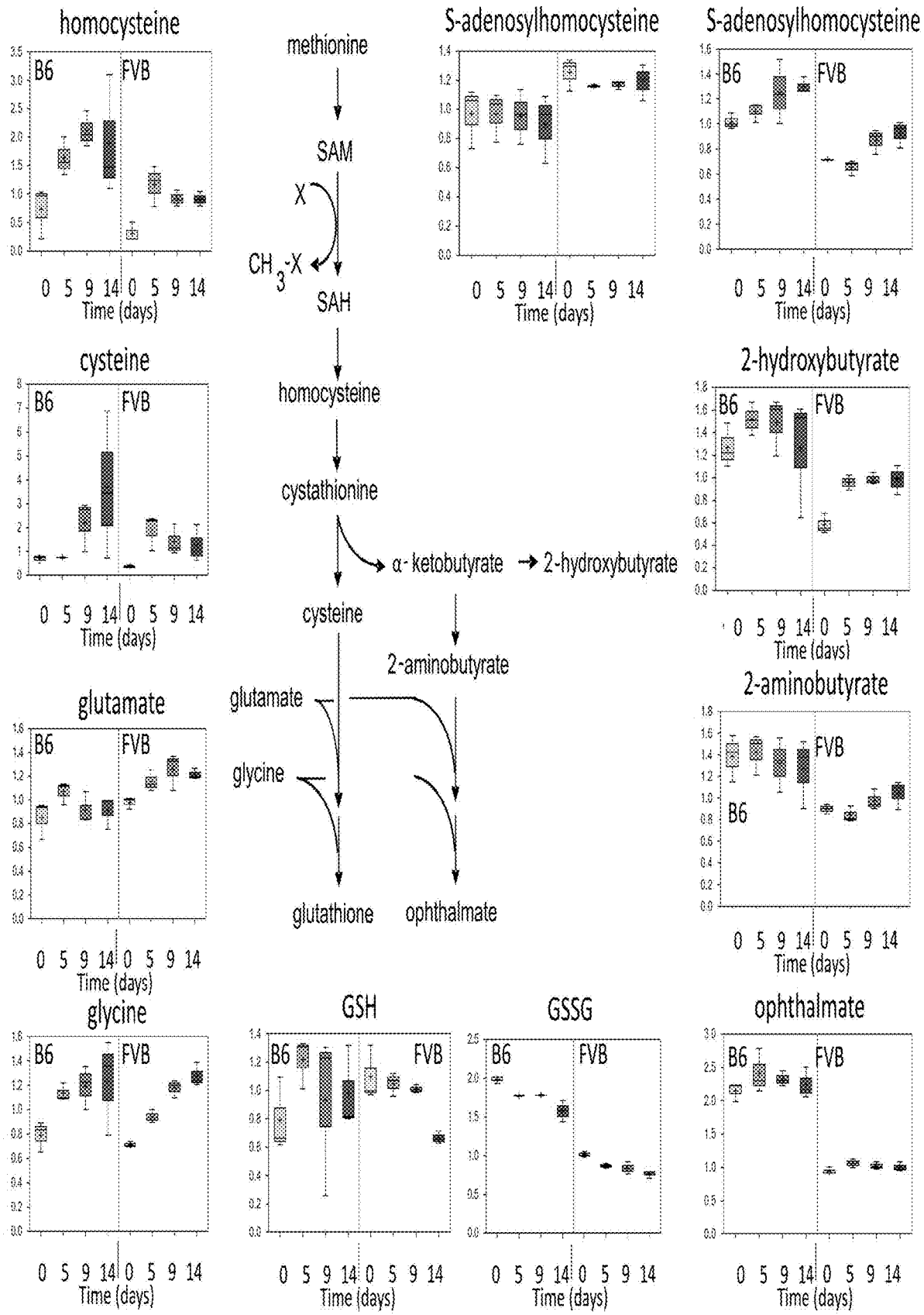
FIG. 2. Metabolomic Analysis of Components of the Glutathione Synthesis and Degradation Pathway During Storage of Murine RBC Units. The same specimens described in FIGS. 1C-1E, were analyzed for components in the glutathione synthesis pathway. These data represent the combined results from 3 separate experiments.

The present invention generally relates to compositions and methods for determining post-transfusion survival and toxicity of RBCs by measuring the levels of one or more markers in a RBC sample.

The invention described in this disclosure represents a method for assessing an RBC unit (prior to transfusion) allowing the prediction of its post-transfusion survival and toxicity. Among the specific aims are: (1) Biochemical markers that predict if RBCs will survive well post-transfusion; and (2) Biochemical markers that predict if RBCs are toxic post-transfusion.

Red blood cell (RBC) transfusion is a life-saving therapy, and refrigerated storage is crucial for maintaining an adequate supply of donor units. However, recent studies have focused on potential adverse clinical sequelae resulting from transfusing humans with RBC units stored for longer periods of time. Indeed, multiple observational studies in human patients provide data demonstrating inferior clinical outcomes when older, stored RBC units are transfused[1]. Nonetheless, this issue remains controversial because other, similarly designed human studies, show no difference in clinical outcome when comparing patients receiving transfusions of older or fresher RBC units[1,2]. To begin to address this controversy, several prospective human trials are currently ongoing, and one was recently completed[3-5]. However, it is not controversial that stored RBCs accumulate multiple factors that may be toxic when infused (e.g. microparticles, free iron, free hemoglobin, prostaglandins, and leukotrienes)[6-4].

One complication in studying RBC transfusion is that there is considerable donor-to-donor variation in the effect of refrigerated storage on RBC function and quality. In addition, there is a general absence of robust analytic tests that consistently and accurately predict the quality of a given RBC unit prior to transfusion[15]. Due to the genetic and environmental complexity of outbred human donor populations, and the difficulty in limiting the number of independent variables in studying human RBC transfusion, we developed a robust animal model to begin to address these issues[16]. Using inbred mouse strains in defined environmental and dietary settings limits the experimental variability of the system, and allows for deliberate manipulation of independent variables. This was combined with metabolomic methods to determine whether variations in the levels, and/or changes in concentrations, of small molecules in vitro correlated with post-transfusion RBC recovery in vivo. In particular, we evaluated whether: 1) genetic background correlated with donor RBC storage quality, 2) metabolomic differences correlated with donor RBC storage quality, and 3) accumulation of potentially toxic molecules correlated with genetic background and/or donor RBC storage quality.

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

As used herein, "RBC storage quality" is defined as the extent of post-transfusion recovery of the stored RBCs; higher recovery is defined as higher quality. Examples of post-transfusion recovery include greater than zero and almost 100% recovery, i.e., recovery of 10%, 20%, 30%, 40%, 50%, 60%, 70%, 80%, 90%, 100%, and all percentages in between. In one embodiment, an acceptable RBC storage quality is an average of 75% post-transfusion recovery at 24 hours, as under FDA guidelines.

As used herein, "toxicity" of a RBC unit is defined as any adverse reaction associated with transfusion of a RBC unit, including, but not limited to, hemolytic transfusion reactions, exposure to free hemoglobin, iron overload, induction of recipient cytokines, introduction of procoagulant activity, and inhibition of recipient vascular relaxation, among others.

As used herein, a RBC unit is less suitable for transfusion if it has lower RBC quality (i.e., post-transfusion survival) or elevated toxicity as compared to other RBC units, e.g., as compared to a control.

An "analyte" or "target" refers to a compound to be detected. Such compounds can include small molecules, peptides, proteins, nucleic acids, as well as other chemical entities. In the context of the present invention, an analyte or target will generally correspond to the biochemical compounds disclosed herein, or a reaction product thereof.

The term "biomarker" refers to a molecule (typically small molecule, protein, nucleic acid, carbohydrate, or lipid) that is expressed and/or released from a cell, which is useful for identification or prediction. Such biomarkers are molecules that can be differentially expressed, e.g., overexpressed or underexpressed, or differentially released in response to varying conditions (e.g., storage). In the context of the present invention, this frequently refers to the biochemical compounds disclosed herein, which are elevated in stored versus non-stored RBCs, for instance, 1-fold, 2-fold, 3-fold, 4-fold, 5-fold or more in stored RBCs versus non-stored RBCs.

A "sample" refers to any source which is suspected of containing an analyte or target molecule. Examples of samples which may be tested using the present invention include, but are not limited to, blood, serum, plasma, urine, saliva, cerebrospinal fluid, lymph fluids, tissue and tissue and cell extracts, cell culture supernatants, among others. A sample can be suspended or dissolved in liquid materials such as buffers, extractants, solvents, and the like. In the context of the present application, a sample is generally a stored RBC sample of varying length of storage.

"Antibody" refers to any immunoglobulin or intact molecule as well as to fragments thereof that bind to a specific epitope that may be used in the practice of the present invention. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term and may be used in the practice of this invention, including IgA, IgD, IgE, IgG, and IgM.

An "antibody fragment" refers specifically to an incomplete or isolated portion of the full sequence of the antibody which retains the antigen binding function of the parent antibody and may also be used in the present invention. Examples of antibody fragments include Fab, Fab', F(ab')2, and Fv fragments; diabodies; linear antibodies; single-chain antibody molecules; and multispecific antibodies formed from antibody fragments.

An intact "antibody" for use in the invention comprises at least two heavy (H) chains and two light (L) chains interconnected by disulfide bonds. Each heavy chain is comprised of a heavy chain variable region (abbreviated herein as HCVR or VH) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a VH domain; and (vi) an isolated complementarity determining region (CDR).

"Single chain antibodies" or "single chain Fv (scFv)" may also be used in the present invention. This term refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments can be prepared by recombinant techniques or enzymatic or chemical cleavage of intact antibodies.

A "monoclonal antibody" may be used in the present invention. Monoclonal antibodies are a preparation of antibody molecules of single molecular composition. A monoclonal antibody composition displays a single binding specificity and affinity for a particular epitope.

In one embodiment, the antibody or fragment is conjugated to an "effector" moiety. The effector moiety can be any number of molecules, including labeling moieties such as radioactive labels or fluorescent labels.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

Samples of RBCs stored for various amounts of time are compared to "control" samples which can be freshly drawn RBCs or RBCs which have been minimally stored. Control samples are assigned a relative analyte amount or activity to which sample values are compared. Relevant levels of analyte elevation occur when the sample amount or activity value relative to the control is 110%, more preferably 150%, more preferably 200-500% (i.e., two to five fold higher relative to the control), more preferably 1000-3000% higher.

Assays for many of the biochemical compounds disclosed herein are known or commercially available.

For example, antibody reagents can be used in assays to detect the levels of analytes in RBC samples using any of a number of immunoassays known to those skilled in the art.

Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., Curr. Opin. Biotechnol., 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (META); immunohistochemical (IHC) assays; capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., Electrophoresis, 18:2184-93 (1997); Bao, J. Chromatogr. B. Biomed. Sci., 699:463-80 (1997). Liposome immunoassays, such as flow-injection liposome immunoassays and liposome immunosensors, are also suitable for use in the present invention. See, e.g., Rongen et al., J. Immunol. Methods, 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., J. Clin. Chem. Clin. Biochem., 27:261-276 (1989)).

Specific immunological binding of the antibody to proteins can be detected directly or indirectly. Direct labels include fluorescent or luminescent tags, metals, dyes, radionuclides, and the like, attached to the antibody. A chemiluminescence assay using a chemiluminescent antibody specific for the protein is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMax® Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

In some embodiments, the measurement of the markers of the present invention is performed using various mass spectrometry methods. As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., Prostate Cancer and Prostatic Diseases 1999, 2: 264-76; and Merchant and Weinberger, Electrophoresis 2000, 21; 1164-67.

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

In some embodiments, the present invention is practiced using computer implementation. In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The following examples of specific aspects for carrying out the present invention are offered for illustrative purposes only, and are not intended to limit the scope of the present invention in any way.

EXAMPLES

Example 1: Materials and Methods

Collection and Processing of Mouse RBC Units

H2-K$^b$ GFP+ mice were a generous gift from Dr. Derek A. Persons (St. Jude Children's Research Hospital; Memphis, Tenn.) and were bred by the Emory University Division of Animal Husbandry by crossing heterozygous mice with C57BL/6J mice in excess of 10 generations[17]; the RBCs of these mice express Green Fluorescent Protein (GFP) and are readily enumerated by flow cytometry. These mice were used as the universal transfusion recipients in all of the described studies. C57BL/6J and FVB/J mice were purchased from The Jackson Laboratory (Bar Harbor, Me.). All mice were housed in identical conditions with identical diets and identical access to water. In an effort to model human RBC storage, mouse donor RBCs were collected and stored in a similar fashion to human RBC storage, as previously described[16]. All studies were carried out under protocols approved by the Institutional Animal Care and Use Committees.

Assessment of Post-Transfusion RBC Recovery and Endogenous RBC Lifespan

For all RBC storage experiments, donor mouse RBCs were stored at 4° C. for 14 days; this time frame was previously identified, using C57/BL6J mouse donor RBCs, as appropriately approximating the refrigerated shelf life identified by the Food and Drug Administration for human RBCs; that is, on average, 75% of donor mouse RBCs were still circulating 24 hr post-transfusion at the Day 14 "outdate.[16]" Therefore, at Day 14 of storage, 100 µl of stored, donor, packed RBCs (i.e. one mouse "unit") were transfused into H2-K$^b$ GFP+ recipient mice. At 10 min, 30 min, 1 hr, 4 hr, and 24 hr post-transfusion, peripheral blood was obtained from recipients, and transfused RBCs were enumerated by flow cytometry by gating on GFP-negative RBC events. Peripheral blood obtained from non-transfused mice was used to enumerate the low number of events in the GFP-negative gate, which were then subtracted from the analysis of transfused RBCs.

For determination of endogenous RBC lifespan, mice received 3 daily injections of NHS-biotin i.p. (Pierce, Thermo Scientific) until ~100% of circulating RBCs were reactive with avidin-allophycocyanin, as assessed by flow cytometry. Peripheral RBCs were then obtained weekly and stained with avidin-allophycocyanin, followed by enumeration of positive and negative RBCs by flow cytometry. These data were then plotted to determine RBC lifespan.

Mass Spectrometry Analysis of RBC Samples

Donor RBC samples, freshly obtained and at various times after refrigerated storage, were rapidly frozen using dry ice/ethanol and stored at 80° C. The supernatant was not stored separately nor were the RBCs washed and stored separately; thus, the results obtained evaluated the metabolites in the entire "unit." Samples were shipped on dry ice to Metabolon Inc., where they were split into equal parts for analysis by gas-chromatography/mass spectrometry (GC/MS) and liquid chromatography-tandem mass spectrometry (LC/MS/MS). The LC/MS/MS platform was based on a Waters ACQUITY UPLC and a Thermo-Finnigan LTQ mass spectrometer, which consisted of an electrospray ionization (ESI) source and linear ion-trap (LIT) mass analyzer. The sample extract was split into two aliquots, dried, and then reconstituted in acidic or basic LC-compatible solvents, each of which contained 11 or more injection standards at fixed concentrations. One aliquot was analyzed using acidic positive-ion optimized conditions and the other using basic negative-ion optimized conditions in two independent injections using separate dedicated columns. Extracts reconstituted in acidic conditions were gradient eluted using water and methanol, both containing 0.1% Formic acid, whereas the basic extracts, which also used water/methanol, contained 6.5 mM Ammonium Bicarbonate. The MS analysis alternated between MS and data-dependent MS$^2$ scans using dynamic exclusion. The samples destined for GC/MS analysis were re-dried under vacuum desiccation for a minimum of 24 hr prior to being derivatized under dried nitrogen using bistrimethyl-silyl-triflouroacetamide. The GC column was 5% phenyl and the temperature ramp was from 40° to 300° C. in a 16 minute period. Samples were analyzed on a Thermo-Finnigan Trace DSQ fast-scanning single-quadrupole mass spectrometer using electron impact ionization. Compounds were identified by comparison to library entries of purified standards or recurrent unknown entities. Identification of known chemical entities was based on comparison to metabolomic library entries of purified standards. As of the time of analysis, more than 1000 commercially-available purified standard compounds had been acquired and registered into LIMS for distribution to both the LC and GC platforms for determination of their analytical characteristics. The combination of chromatographic properties and mass spectra gave an indication of a match to the specific compound or an isobaric entity.

The peak areas for each identified biochemical entity were log transformed, scaled to the median value for each compound observed in the experiment, and normalized to Bradford protein content; results below the limit of detection were imputed with the minimum observed value for the compound. A Two-Way ANOVA with Contrasts was used to determine the significance of variable main effects (e.g. Condition or Time/Day) and their interaction, and to identify biochemical entities that differed significantly between experimental groups ($p<0.05$). An estimate of the false discovery rate (q-value) is calculated to take into account the multiple comparisons that normally occur in metabolomic-based studies.

Example 2: Variation Among Inbred Mouse Strains in Post-Transfusion RBC Recovery after Refrigerated Storage As used herein, "RBC storage quality" is defined as the extent of post-transfusion recovery of the stored RBCs; higher recovery is defined as higher quality. Thus, to test the hypothesis that donor-specific variation in RBC quality after refrigerated storage exists in non-human systems, mice were chosen as the experimental model. After screening 6 common inbred laboratory strains of mice from Jackson labs (C57BL6/J, FVB/J, C3H/J, BALBc/J, SJL/J, DBA2/J) and observing variation in RBC storage quality between strains (data not shown), we focused our studies on a direct comparison of the one that exhibited the best storage quality (C57BL/6J; i.e. B6), and the one that exhibited the worst RBC storage quality (FVB/NJ; i.e. FVB). To this end, peripheral blood RBCs were obtained from B6 and FVB mice, filter leukoreduced, stored for 14 days, transfused, and evaluated for post-transfusion recovery using a method that models human RBC storage[16]; these prior studies demonstrated that 14 days of storage provided results with B6 RBCs that mimicked those found with healthy human blood donors after 42 days of storage (i.e. ~75% post-transfusion recovery). To allow post-transfusion tracking without labeling or otherwise modifying the donor RBCs, a single strain of recipient mice was utilized that expressed transgenic GFP in their RBCs; in this way, no artifactual damage to the donor RBCs was introduced by any further pre-transfusion manipulation or any labeling process. The circulating, transfused donor RBCs were then quantified by flow cytometry by gating on the GFP-negative population.

RBCs from each donor strain were stored at the same hematocrit, and the same volume of RBCs was transfused from each strain into naïve recipients. All donor RBCs were transfused intravenously through the tail vein. As is typically the case when transfusing stored human or murine RBCs into either human or murine recipients, respectively, there was a rapid clearance phase followed by a significantly slower clearance phase (FIG. 1A). The early phase clearance in humans has been interpreted as the rapid extravascular clearance of significantly storage-damaged RBC[18], which has been demonstrated to be the case in mice, since depletion of phagocytes prevents the early clearance from occurring[11]. At 10 min post-transfusion, approximately 40% fewer transfused FVB RBCs were still circulating in peripheral blood, as compared with transfused B6 RBCs (FIG. 1A). This statistically significant difference persisted over time, with FVB RBCs having only ~50% of the 24-hour post-transfusion recovery of B6 RBCs (FIG. 1A). The post-transfusion recovery of 14-day old B6 RBCs was comparable to that seen previously[16]. Taken together, these data demonstrate a strain-specific difference in donor RBC storage quality and suggest that a genetic difference(s) may account for the observed effects.

To test if RBC quality after refrigerator storage in vitro correlated with the endogenous RBC lifespan in the donor mice in vivo, the total blood volumes of B6 and FVB mice were each labeled by biotinylation in vivo. In this method, any new RBCs that are generated do not have biotin on their surface; thus, RBC lifespan can be determined by the rate of decrease of avidin-reactive RBCs over time[19]. Using this approach, FVB RBCs had a shorter endogenous lifespan as compared to B6 RBCs, correlating with the trend seen in refrigerated RBC storage quality (FIG. 1B). However, the natural differences in endogenous lifespan were not as pronounced as the differences in post-transfusion recovery of stored RBCs. Taken together, these data demonstrate strain-dependent differences in endogenous RBC lifespan, which correlate with amplified differences in post-transfusion recovery resulting from refrigerated RBC storage.

Example 3: Analysis of Anti-Oxidant Pathways and Accumulation of Oxidative Damage During RBC Storage Mass spectrometric analysis captured multiple types of metabolites that were tracked during storage. Disclosed herein are several illustrative types of metabolites and their associated biosynthetic and catabolic pathways. Levels of 9,10 epoxystearate (as an indicator of lipid oxidation) increased progressively in refrigerator-stored FVB RBC units, but remained largely at baseline levels in stored B6 RBC units (FIG. 1C). Likewise, oxidation of cholesterol into both 7-alpha-hydroxycholesterol and 7-beta-hydroxycholesterol, and their subsequent conversion into 7-ketocholesterol, progressively increased in FVB RBC units, but not in B6 units (FIG. 1C). However, cholesterol levels in both FVB and B6 units did not differ and did not change significantly with storage time. Taken together, these data demonstrate that increased lipid oxidation correlated with poor storage quality of FVB RBCs.

Reduced glutathione (GSH) is generally considered to be the most robust anti-oxidant in RBCs. Although no statistically significant differences in GSH levels were observed when comparing stored RBC units from B6 and FVB mice (FIG. 1D), B6 RBC units had consistently higher levels of oxidized glutathione (GSSG) and cysteine-glutathione disulfides (FIG. 1D); the latter also increased progressively with storage in B6 units. In addition, although levels of the natural anti-oxidant alpha-tocopherol (i.e. Vitamin E) were equivalent at the time of blood collection, alpha-tocopherol levels dropped rapidly in FVB, but not B6, RBC units (FIG. 1E). Moreover, levels of another anti-oxidant, ergothioneine, were significantly higher on the day of collection in B6 RBC units, as compared to FVB RBC units (FIG. 1E); these levels also increased during storage in B6, but not FVB, RBC units.

Analysis of multiple components of the GSH biosynthetic pathway revealed that B6 RBC units accumulated higher levels of homocysteine and cysteine during storage, as compared to FVB RBC units (FIG. 2); these could potentially provide more substrate for GSH synthesis de novo in the RBC units by combining with glutamate and glycine. Nonetheless, no differences in glutamate or glycine levels were observed when comparing FVB and B6 RBC units, either at baseline or during storage. In addition, the sum of GSH and GSSG levels was higher in B6, as compared to FVB, RBC units. Finally, as compared with FVB RBC units, B6 RBC units had significantly higher levels of byproducts of GSH synthesis, including 2-hydroxybutyrate, 2-aminobutyrate, and ophthalmate (FIG. 2). Interestingly, accumulation of ophthalmate was previously reported to reflect GSH consumption in an effort to ameliorate oxidative stress[20]. Taken together, these results suggest that there may be greater flux through the GSH pathway in B6 RBC units, and that RBC storage quality correlates positively with an enhanced ability to handle oxidative stress.

Figure 3A:
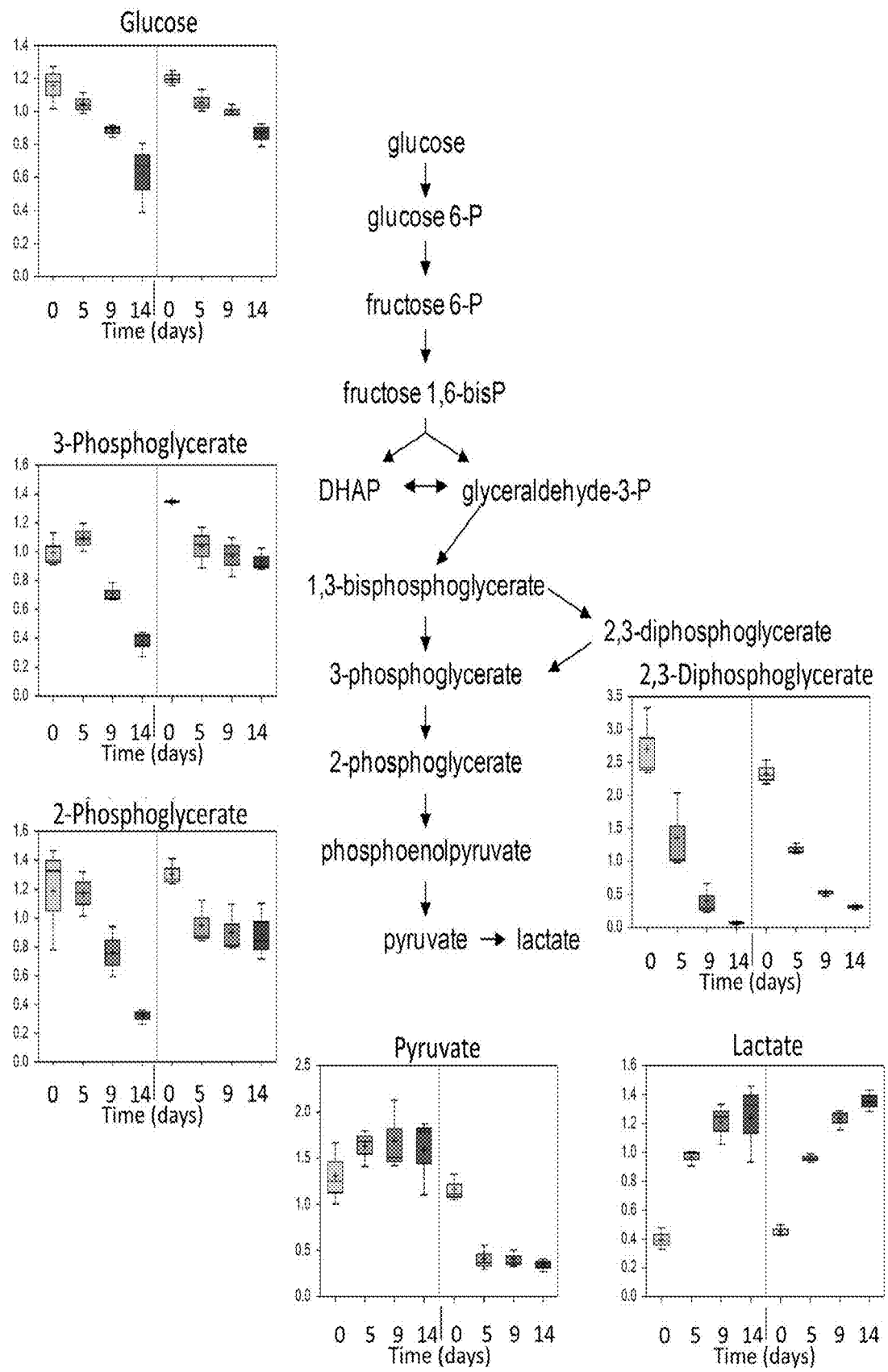
FIGS. 3A, 3B. Metabolomic Analysis of Components of the Glycolytic and Purine Metabolic Pathways During Storage of Murine RBC Units. The same specimens described in FIGS. 1C-1E, were analyzed for components of the glycolytic (FIG. 3A) and purine metabolic (FIG. 3B). These data represent the combined results from 3 separate experiments.

Example 4: Evaluation of Glycolysis and Purine Metabolism During RBC Storage When glycolytic pathways were analyzed (FIG. 3A), the results were similar to what has been repeatedly reported regarding refrigerated storage of human RBCs[6]. In particular, glucose and 2,3-DPG levels progressively declined, whereas lactate levels progressively increased in stored RBC units from both mouse strains. In contrast, pyruvate levels increase and remain elevated during storage of B6, as compared to FVB, RBC units.

Figure 3B:
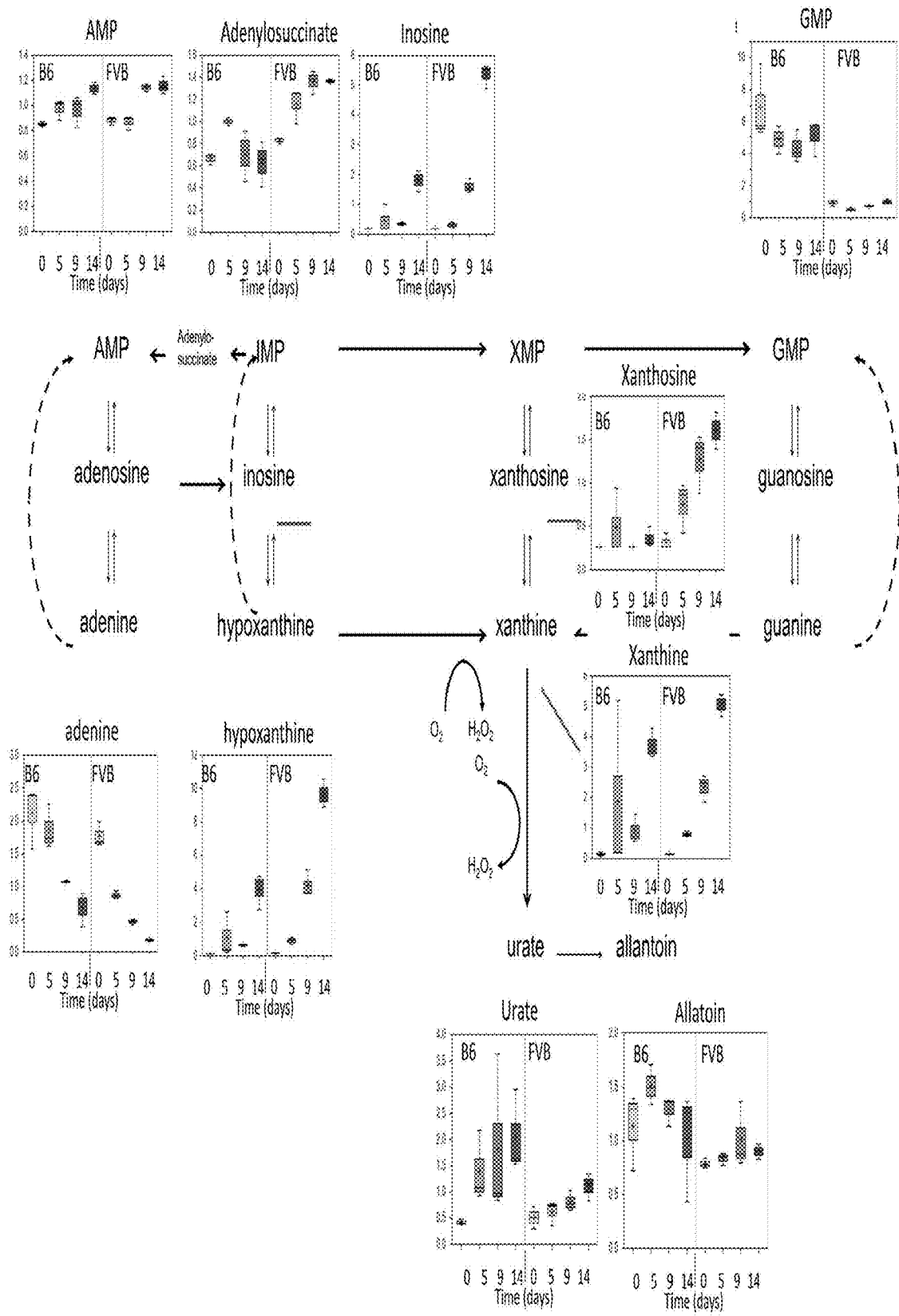

Because adenine is a component of various RBC storage solutions (e.g. CPDA-1), its initial levels in RBC units are high due to this supplementation. During refrigerated storage, adenine progressively declined, and AMP levels slowly increased, similarly in both B6 and FVB RBC units (FIG. 3B). Inosine, into which adenine can be converted, increased steadily over storage time in RBC units from both mouse strains, but with higher levels in FVB RBC units. Both hypoxanthine and xanthine increased significantly over time, with higher endpoint levels in FVB, as compared to B6, RBC units; these results suggest that a substantial quantity of inosine can be metabolized in a way that prevents subsequent ATP synthesis. Urate levels were also higher in B6, as compared to FVB, RBC units, and levels of allantoin (the main breakdown product of urate) remained relatively stable in both B6 and FVB RBC units.

Example 5: Accumulation of Eicosanoids During RBC Storage

Figure 4:
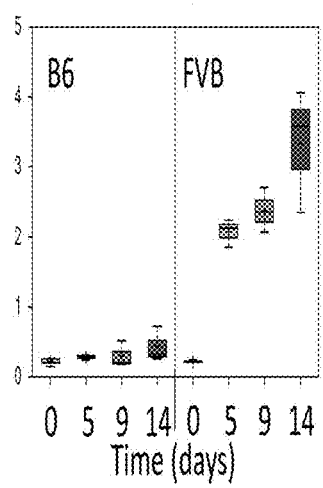
FIG. 4. Arachidonic Acid and Eicosanoid Levels in Stored Murine RBC Units, as Measured by Metabolomic Analysis. The same specimens described in FIGS. 1C-1E were analyzed for determining levels of arachidonic acid and various eicosanoids. These data represent the combined results from 3 separate experiments.
Figure 4:
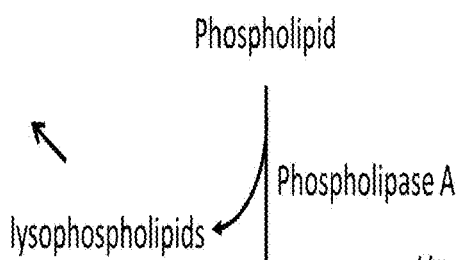
Figure 4:
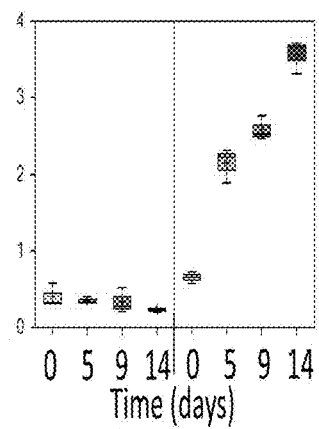
Figure 4:
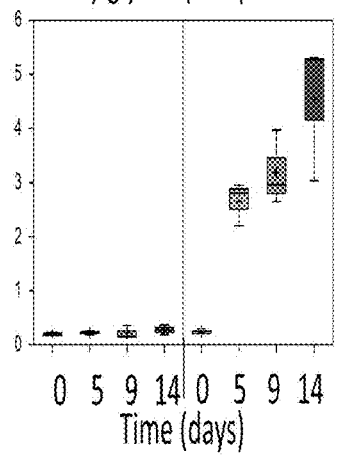
Figure 4:
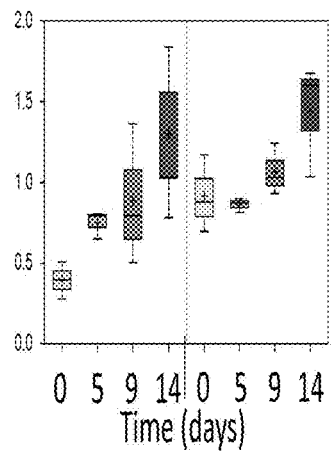
Figure 4:
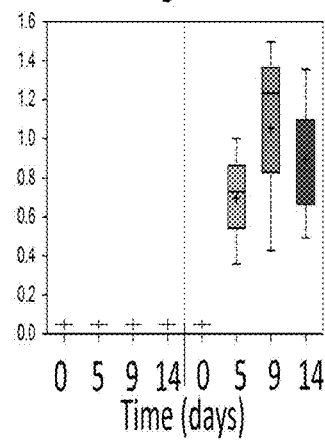
Figure 4:
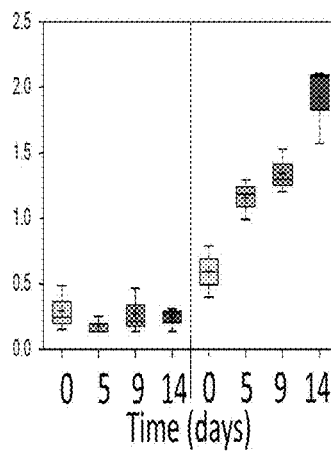
Figure 4:
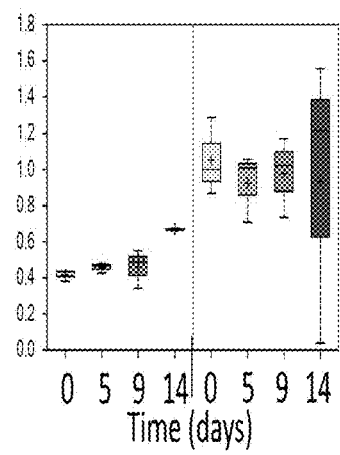
Figure 4:
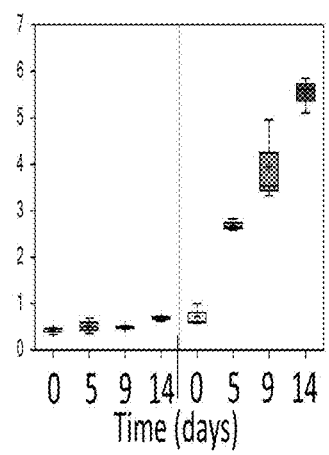

The RBC membrane is a rich source of phospholipids, and the oxidation and/or enzymatic processing of these can produce arachidonic acid, which, in turn, can be converted into prostaglandins and/or leukotrienes (the latter, together, are termed eicosanoids). Eicosanoids have potent and widespread effects on inflammation, vascular tone, vascular permeability, and platelet activation[21-23]. Interestingly, arachidonic acid (or, equivalently, arachidonate) accumulated progressively during storage of both B6 and FVB RBC units (FIG. 4). Although baseline levels were significantly higher in FVB RBC units, peak levels at Day 14 were equivalent in both strains. The source of arachidonic acid in this setting is likely to be phospholipase-induced release of fatty acids from the sn-2 position of inositol-containing phospholipids. However, unlike the similar levels of arachidonic acid, there was a substantial increase in lysophospholipid by-products (i.e. 1-palmitoylglycerophosphoinositol and 1-stearoylglycerophosphoinositol) in FVB, but not B6, RBC units. There was also a dramatic accumulation of eicosanoids during storage of FVB, but not B6, RBC units. The latter included prostaglandin E2 and several leukotriene precursors (i.e. 5-HETE, 12-HETE, and 15-HETE). In addition, in FVB RBC units, the levels of linoleic acid metabolites (i.e. 13-HODE and 9-HODE) significantly increased during storage; in contrast, these remained low in B6 RBC units. Together, these data suggest that there is increased generation and metabolism of arachidonic acid in FVB RBC units, with concomitant increases in the synthesis of multiple eicosanoids during storage of these units.

Example 6: Pyrimidine Metabolism During RBC Storage

Figure 5:
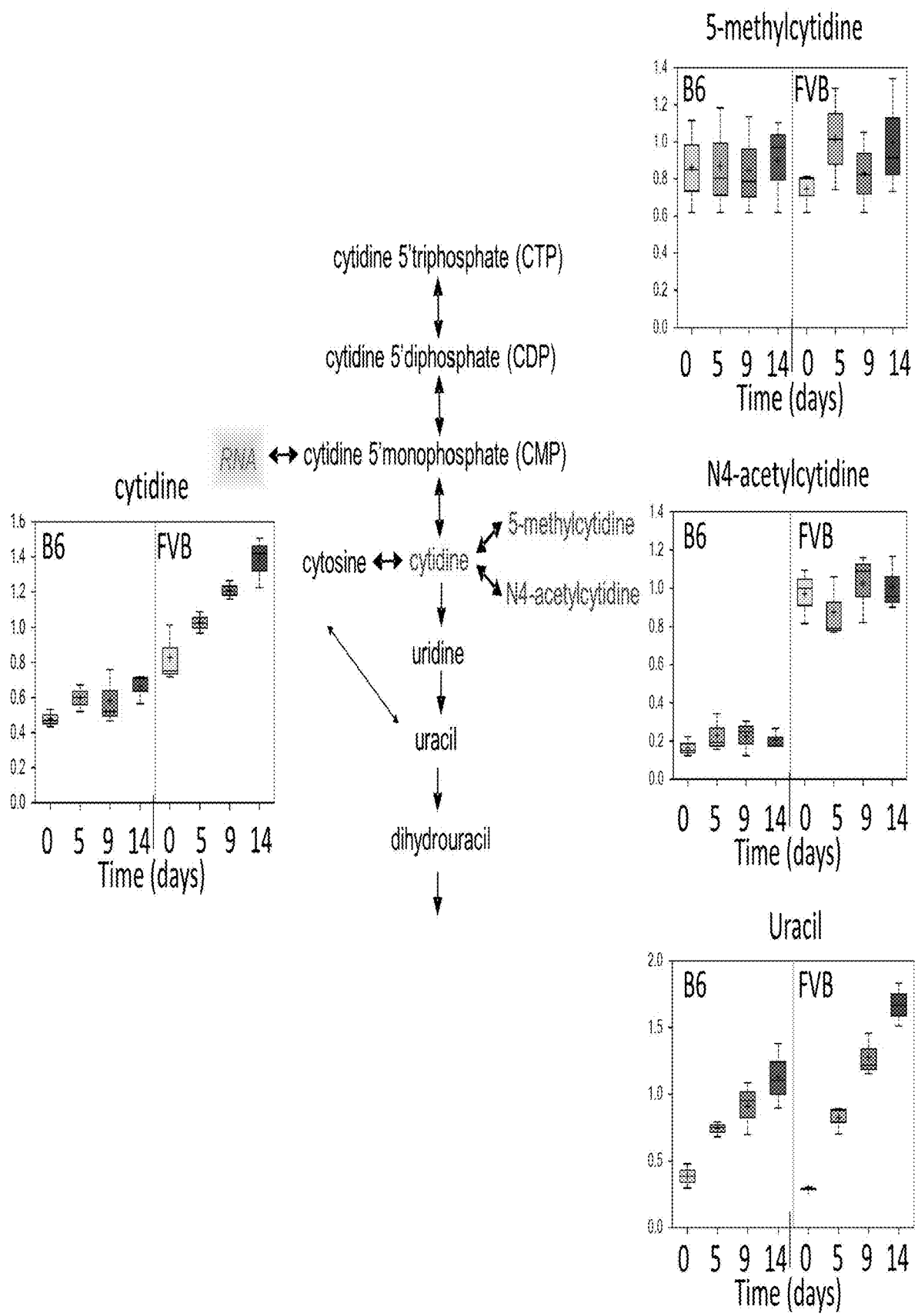
FIG. 5. Pyrimidine Metabolism in Murine RBC Units with Differential Storage Biology. The same murine specimens described in FIGS. 1A-1E were analyzed for cytidine metabolism (cytidine, 5-methylcytidine, and N4-acetylcytidine). These data represent the combined results from 3 separate experiments.

Assessment of pyrimidine metabolism demonstrated that FVB RBC units had higher levels of cytidine at baseline, as compared to those obtained from B6 mice (FIG. 5). In addition, during storage, cytidine levels increased to a significantly greater extent in FVB, as compared to B6, RBC units. Levels of N4-acetylcytidine (a cytidine metabolite) were also approximately 8-fold higher, at all time points measured, in FVB compared to B6 RBC units (FIG. 5). Finally, the levels of one downstream metabolite, uracil, were significantly greater in FVB than B6 RBC units at end of storage; however, no differences were observed in the levels another metabolite, 5-methylcytidine.

Example 7: Application of Markers as a Diagnostic Test of RBCs

As a result of the studies above, we have identified a distinct panel of metabolites that predicts how well stored RBCs will survive post-transfusion. This panel includes members of pyrimidine metabolism, cytidine and its breakdown products. These include: Cytidine, 5-Methylcytidine, N4-acetylcytidine. A further panel includes markers that indicate the generation of inflammatory eicosanoids. These include: 9-HODE, 13-HODE, Prostaglandin E2, 5-HETE, 12-HETE, 15-HETE, arachidonic acid, 1-palmitoylglycerophosphoinositol, 1-stearoylglycerophosphoinositol, and 13, 14-dihydro-15-keto-prostaglandin E2.

The above markers of RBC unit quality may be applied to evaluation of RBC units in several different ways. First, a sample of an RBC unit can be subjected to mass spectrometry and the profile of the above markers can be generated (all from a single sample). This profile would then be used to predict the post-transfusion survival of the RBC unit. Such information would allow two distinct medical advantages: 1) direction of better units of RBCs to patients whose disease status makes them particularly susceptible to toxicity of poorly stored RBC units, and 2) management of the blood supply such that storage time for individual units could be tailored to the biology of the unit. Moreover, it is possible that FDA guidelines could be tailored to utilize these specific chemical measurements as release criteria for RBC units. In one embodiment, a high throughput mass spectrometer is used. Alternatively, individual assays could be run on a much smaller platform by traditional assay techniques (i.e. ELISA, enzymatic assay, etc.). Such would allow a simplified platform with a less expensive instrumentation. For such purposes, a small number of the above chemical entities that were representative of the whole would be identified and measured.

With respect to cytidine as a marker, it is noted that the in vivo lifespan of FVB RBCs was shorter than that of C57BL/6 (B6), which correlates with the trend in RBC storage biology—FVB RBCs store more poorly than do B6 RBCs. In addition, it is observed that the FVB RBCs that store more poorly have increased levels of cytidine, and this correlation was also observed on human RBCs. Based upon the new in vivo data, we raise the possibility that FVB mice had higher reticulocyte counts than did B6, as a compensatory mechanism for shorter RBC lifespan, so as to maintain normal hematocrit levels. Since reticulocytes are a rich source of RNA, which can then be broken down into cytidine, this constitutes a novel explanatory hypothesis for the observed biology.

Patients whose RBCs store poorly have shorter natural in vivo RBC lifespan (as a result of their intrinsic biology). As a result of shorter RBC lifespan, they make RBCs more quickly, and thus have higher reticulocyte counts. As a result of higher reticulocyte count, they have higher RNA in the unit. As a result of higher RNA in the unit, they have higher levels of cytidine. This explanation suggests that cytidine is a correlative marker of someone who has RBCs with an intrinsically shorter lifespan. This does not speak to mechanism, and suggests that cytidine is just a correlative marker. However, if this association turns out to be true, then the reticulocyte count itself should be equally predictive. Thus, this line of reasoning leads to the following aim. Measuring reticulocyte count of a blood donor at the time of donation will predict how well the RBCs will store and how well they will circulate after transfusion.

Thus, reticulocyte counts, which are routinely determined in the hospital, can be used as an indicator of RBC storage quality. In particular, patients with underlying pathology for which it would be predicted that poorly storing RBCs would be particularly dangerous would selectively get RBCs from donors that had low reticulocyte count at time of donation.

DISCUSSION

The data presented herein demonstrate that different inbred strains of mice (i.e. B6 and FVB) have significant differences in RBC storage quality (defined as post-transfusion RBC recovery), which is the gold standard for evaluating the storage of human RBC donor units. Because post-transfusion RBC clearance depends on the storage quality of the RBCs themselves, as well as on the activity of the recipient's mononuclear phagocyte system, we used one mouse strain as the universal transfusion recipient for these studies (i.e. GFP transgenic mice on a B6 background). This experimental design decreases concerns regarding differences in RBC clearance biology in the recipient, allowing an exclusive focus on the storage of the donor RBC units. Although this approach could raise the concern that the B6 transfusions were syngeneic, whereas the FVB transfusions were allogeneic, the 24-hr RBC recovery assay is complete long before adaptive immunity is induced. In addition, B6 mice have no "naturally-occurring" antibodies that recognize FVB RBC antigens as tested by flow cytometry, both in vitro and in vivo (data not shown). Moreover, there is no difference when B6xFVB F1 recipients are used, the storage quality of B6 RBCs is significantly better than FVB RBCs (data not shown). Finally, the described accumulation of oxidative damage (FIGS. 1A-1E) and eicosanoids (FIG. 4) occurs in vitro during storage prior to transfusion; thus, these effects are unrelated to potential allogenicity in vivo. Taken together, these data describe strain-specific variations in donor RBC storage quality, and suggest that this variation is caused, at least in part, by genetic determinants.

The current results with stored mouse RBC units suggest that oxidative damage increases with storage duration, particularly for FVB mice (FIG. 1C). In addition, levels of two endogenous anti-oxidants (i.e. alpha-tocopherol and ergothioneine) are maintained at higher levels in B6, as compared to FVB, stored RBCs units (FIG. 1E). Although the results for the GSH biosynthetic pathway are more complex (FIG. 1D and FIG. 2), one explanation that is consistent with the current data posits that synthesis and flux through this pathway is greater in stored B6 RBC units, thereby allowing these units to handle oxidative stress more effectively than those obtained from FVB mice. In addition, the findings presented in FIGS. 1A-1E and 2 are consistent with a previous report of oxidative stress-induced hemolysis in inbred mouse strains; in this setting, B6 RBCs exhibited decreased $H_2O_2$-induced injury, as compared to RBCs obtained from other strains; however, FVB mice were not studied[24]. Finally, an important role for oxidative stress and glutathione in the biology of RBC storage has been described previously, particularly with regard to human RBC storage[25-27].

Recently, eicosanoids have been reported to accumulate during storage of human RBC units. The same molecular species as we observed in FVB RBC units were reported in human units (i.e. Arachidonic acid, 5-HETE, 12-HETE, and 15-HETE)[13]; however, prostaglandin increase was not noted. To the best of our knowledge, the work disclosed herein is the first demonstration of substantial donor variation (in mice) regarding the accumulation of eicosanoids during RBC storage, and also the first indication that this variation may have a genetic basis in any species. In FVB RBC units, the maintenance of arachidonic acid levels during storage, in the context of increasing levels of lysophospholipids and eicosanoids, suggests a rapid flux through this pathway (in terms of arachidonic acid generation and its subsequent conversion into downstream products). In contrast, although arachidonic acid levels increase during storage of B6 RBC units, there is little generation of lysophospholipids or conversion to eicosanoids. Taken together, these results suggest the testable hypothesis that FVB RBC units have higher phospholipase, cyclooxygenase, and lipoxygenase activities, as compared to B6 RBC units. It is worth noting that C57BL/6 mice are deficient in a secreted phospholipase A2 (sPLA2), which may explain increased arachidonic acid generation in FVB mice. However, this would not explain the increased conversion into prostaglandins and leukotrienes, which would require other differences in cyclooxygenase and lipoxygenase activities. Of particular note is that analysis of human RBC units have not detected cellular or soluble phospholipase activity (cPLA2 and sPLA2 were not detected)[28]. Rather, an alternate source of phospholipase has been implicated, in particular, peroxiredoxin-6[28].

While the above changes have been noted in "stored RBC units", neither the location (e.g. cellular or supernatant) nor the source (e.g. the RBCs themselves, residual leukocytes, or contaminating platelets) is determined by the current methodologies. Although leukoreduction results in a unit with essentially undetectable leukocytes, it seems likely that some remain. Moreover, platelets are far more numerous in mice than in humans, and while leukoreduction does decrease murine platelets in RBC units, significant numbers of detectable platelets persist (data not shown). Accordingly, while RBCs may turn out to be the source of eicosanoids, it would be premature and potentially incorrect to draw any inferences that the RBCs are the source of eicosanoids from the current studies. Nevertheless, regardless of the cellular source, the observation of dramatic differences between genetically distinct strains persists.

Long-term dietary and/or environmental factors could affect RBC storage quality. Indeed, the results of the classical human studies of Dern et al. could be due to heritable factors or long-term dietary behavior and/or environmental exposure[29]. In the current study, control over variation in acquired factors which may influence RBC storage was attempted in a controlled laboratory environment. All animals were females of the same age, were provided the same commercial mouse chow ad libitum and were housed in the same vivarium with identical sources of bedding, water, and caging.

SUMMARY

In summary, RBC transfusion is a life-saving therapy, the logistical implementation of which requires RBC storage. However, stored RBCs exhibit substantial donor variability in multiple characteristics, including hemolysis in vitro and RBC recovery in vivo. The basis of donor variability is poorly understood.

We applied a murine model of RBC storage and transfusion to test the hypothesis that genetically distinct inbred strains of mice would demonstrate strain-specific differences in RBC storage. In vivo recoveries were determined by monitoring transfused RBCs over 24 hours. Timed aliquots of stored RBCs were subjected to tandem chromatography/mass spectrometry analysis to elucidate metabolic changes in the RBCs during storage.

Using independent inbred mouse strains as donors, we found substantial strain-specific differences in post-transfusion RBC recovery in vivo following standardized refrigerated storage in vitro. Poor post-transfusion RBC recovery correlated with reproducible metabolic variations in the stored RBC units, including increased lipid peroxidation, decreased levels of multiple natural antioxidants, and accumulation of cytidine. Strain-dependent differences were also observed in eicosanoid generation (i.e. prostaglandins and leukotrienes).

These findings provide the first evidence of strain-specific metabolomic differences following refrigerated storage of murine RBCs. They also provide the first definitive biochemical evidence for strain specific variation of eicosanoid generation during RBC storage. The molecules described that correlate with RBC storage quality, and their associated biochemical pathways, suggest multiple causal hypotheses that can be tested regarding predicting the quality of RBC units prior to transfusion and developing methods of improved RBC storage.

REFERENCES 1. van de Watering L. Red cell storage and prognosis. Vox Sang 2011; 100: 36-45.
2. van de Watering L. Pitfalls in the current published observational literature on the effects of red blood cell storage. Transfusion 2011; 51: 1847-1854.
3. Fergusson D A, Hebert P, Hogan D L, LeBel L, Rouvinez-Bouali N, Smyth J A, Sankaran K, Tinmouth A, Blajchman M A, Kovacs L, Lachance C, Lee S, Walker C R, Hutton B, Ducharme R, Balchin K, Ramsay T, Ford J C, Kakadekar A, Ramesh K, Shapiro S. Effect of fresh red blood cell transfusions on clinical outcomes in premature, very low-birth-weight infants: the ARIPI randomized trial. JAMA 2012; 308: 1443-1451.
4. Lacroix J, Hebert P, Fergusson D, Tinmouth A, Blajchman M A, Callum J, Cook D, Marshall J C, McIntyre L, Turgeon A F. The Age of Blood Evaluation (ABLE) randomized controlled trial: study design. Transfus Med Rev 2011; 25: 197-205.
5. Steiner M E, Assmann S F, Levy J H, Marshall J, Pulkrabek S, Sloan S R, Triulzi D, Stowell C P. Addressing the question of the effect of RBC storage on clinical outcomes: the Red Cell Storage Duration Study (RECESS) (Section 7). Transfus Apher Sci 2010; 43: 107-116.
6. Hess J R. Red cell changes during storage. Transfus Apher Sci 2010; 43: 51-59.
7. Hess J R. Red cell storage. J Proteomics 2010; 73: 368-373.
8. Hod E A, Brittenham G M, Billote G B, Francis R O, Ginzburg Y Z, Hendrickson J E, Jhang J, Schwartz J, Sharma S, Sheth S, Sireci A N, Stephens H L, Stotler B A, Wojczyk B S, Zimring J C, Spitalnik S L. Transfusion of human volunteers with older, stored red blood cells produces extravascular hemolysis and circulating non-transferrin-bound iron. Blood 2011; 118: 6675-6682.
9. Hod E A, Spitalnik S L. Harmful effects of transfusion of older stored red blood cells: iron and inflammation. Transfusion 2011; 51: 881-885.
10. Hod E A, Spitalnik S L. Stored red blood cell transfusions: Iron, inflammation, immunity, and infection. Transfus Clin Biol 2012; 19: 84-89.
11. Hod E A, Zhang N, Sokol S A, Wojczyk B S, Francis R O, Ansaldi D, Francis K P, Della-Latta P, Whittier S, Sheth S, Hendrickson J E, Zimring J C, Brittenham G M, Spitalnik S L. Transfusion of red blood cells after prolonged storage produces harmful effects that are mediated by iron and inflammation. Blood 2010; 115: 4284-4292.
12. Kor D J, Van Buskirk C M, Gajic O. Red blood cell storage lesion. Bosn J Basic Med Sci 2009; 9 Suppl 1: 21-27.
13. Silliman C C, Moore E E, Kelher M R, Khan S Y, Gellar L, Elzi D J. Identification of lipids that accumulate during the routine storage of prestorage leukoreduced red blood cells and cause acute lung injury. Transfusion 2011; 51: 2549-2554.
14. Tissot J D, Rubin O, Canellini G. Analysis and clinical relevance of microparticles from red blood cells. Curr Opin Hematol 2010; 17: 571-577.
15. Dumont L J, AuBuchon J P. Evaluation of proposed FDA criteria for the evaluation of radiolabeled red cell recovery trials. Transfusion 2008; 48: 1053-1060.
16. Gilson C R, Kraus T S, Hod E A, Hendrickson J E, Spitalnik S L, Hillyer C D, Shaz B H, Zimring J C. A novel mouse model of red blood cell storage and post-transfusion in vivo survival. Transfusion 2009; 49: 1546-1553.
17. Dominici M, Tadjali M, Kepes S, Allay E R, Boyd K, Ney P A, Horwitz E, Persons D A. Transgenic mice with pancellular enhanced green fluorescent protein expression in primitive hematopoietic cells and all blood cell progeny. Genesis 2005; 42: 17-22.
18. Klein H G, Anstee D J. Mollisoni's Blood Transfusion in Clinical Medicine. Malden, Mass: Blackwell Publishing Inc, 2005.
19. Hoffmann-Fezer G, Maschke H, Zeitler H J, Gais P, Heger W, Ellwart J, Thierfelder S. Direct in vivo biotinylation of erythrocytes as an assay for red cell survival studies. Ann Hematol 1991; 63: 214-217.
20. Soga T, Baran R, Suematsu M, Ueno Y, Ikeda S, Sakurakawa T, Kakazu Y, Ishikawa T, Robert M, Nishioka T, Tomita M. Differential metabolomics reveals ophthalmic acid as an oxidative stress biomarker indicating hepatic glutathione consumption. J Biol Chem 2006; 281: 16768-16776.
21. Aoki T, Narumiya S. Prostaglandins and chronic inflammation. Trends Pharmacol Sci 2012; 33: 304-311.
22. Di Gennaro A, Haeggstrom J Z. The leukotrienes: immune-modulating lipid mediators of disease. Adv Immunol 2012; 116: 51-92.
23. Pratico D, Dogne J M. Vascular biology of eicosanoids and atherogenesis. Expert Rev Cardiovasc Ther 2009; 7: 1079-1089.
24. Kruckeberg W C, Doorenbos D I, Brown P O. Genetic differences in hemoglobin influence on erythrocyte oxidative stress hemolysis. Blood 1987; 70: 909-914.
25. Dumaswala U J, Wilson M J, Wu Y L, Wykle J, Zhuo L, Douglass L M, Daleke D L. Glutathione loading prevents free radical injury in red blood cells after storage. Free Radic Res 2000; 33: 517-529.
26. Dumaswala U J, Zhuo L, Jacobsen D W, Jain S K, Sukalski K A. Protein and lipid oxidation of banked human erythrocytes: role of glutathione. Free Radic Biol Med 1999; 27: 1041-1049.
27. Dumaswala U J, Zhuo L, Mahajan S, Nair P N, Shertzer H G, Dibello P, Jacobsen D W. Glutathione protects chemokine-scavenging and antioxidative defense functions in human RBCs. Am J Physiol Cell Physiol 2001; 280: C867-C873.
28. Silliman C C. Lipids: Free Fatty Acids, Eicosanoids, and Lysophospholipids and the Pro-Inflammatory Effects of Transfusion ASH Meeting 2012 Scientific Program 2012: SCI-48.
29. Dern R J, Wiorkowski J J. Studies on the preservation of human blood. IV. The hereditary component of pre- and poststorage erythrocyte adenosine triphosphate levels. J Lab Clin Med 1969; 73: 1019-1029.
30. Mouse Phenome Database [monograph on the internet]. 2012. Available from: World Wide Web at phenome.jax.org/

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

The invention claimed is:
1. A method of determining blood transfusion suitability of a red blood cell (RBC) unit, the method comprising:
measuring levels of markers 9-HODE, 13-HODE, 5-HETE, 12-HETE, and 15-HETE in a RBC unit;
comparing the levels of the measured markers in the RBC unit with levels of corresponding markers present in a control RBC unit determined to be suitable for use in a blood transfusion; and
using the RBC unit in a blood transfusion when an equal or lower level of each measured marker in the RBC unit compared to the corresponding marker in the control RBC unit is determined; or excluding the RBC unit from use in a blood transfusion or discarding the RBC unit when a higher level of each measured marker in the RBC unit compared to the corresponding marker in the control RBC unit is determined.

2. The method according to claim 1, wherein the method comprises measuring levels of markers 9-HODE, 13-HODE, 5-HETE, 12-HETE, 15-HETE, and arachidonic acid.

3. The method according to claim 1, wherein the levels of the markers are measured by performing mass spectrometry.

4. The method according to claim 3, wherein the mass spectrometry is gas-chromatography/mass spectrometry (GC/MS) or liquid chromatography-tandem mass spectrometry (LC/MS/MS).

5. The method according to claim 1, wherein the levels of the markers are measured by performing an ELISA.

6. The method according to claim 1, wherein the levels of the markers are measured by performing an enzymatic assay.

7. The method according to claim 1, wherein the higher level of each marker in the excluded or discarded RBC unit is 2-200 fold higher than the corresponding marker in the control RBC unit.

8. The method according to claim 1, wherein comparing the levels of the measured markers further comprises predicting post-transfusion survival of red blood cells of the RBC unit based on the compared levels.

9. The method according to claim 1, wherein 75% or greater of red blood cells in the RBC unit used in the blood transfusion are still circulating 24 hours post-transfusion.

* * * * *